US009700509B2

(12) United States Patent
Göpferich et al.

(10) Patent No.: US 9,700,509 B2
(45) Date of Patent: Jul. 11, 2017

(54) SOLUTIONS OF LIPOPHILIC SUBSTANCES, ESPECIALLY MEDICINAL SOLUTIONS

(75) Inventors: Achim Göpferich, Sinzing (DE); Christoph Luschmann, Schmidmühlen (DE)

(73) Assignee: UNIVERSITÄT REGENSBURG, Regensburg (DE)

( * ) Notice: Subject to any disclaimer, the term of this patent is extended or adjusted under 35 U.S.C. 154(b) by 0 days.

(21) Appl. No.: 13/130,361

(22) PCT Filed: Nov. 27, 2009

(86) PCT No.: PCT/EP2009/065982
§ 371 (c)(1),
(2), (4) Date: Aug. 2, 2011

(87) PCT Pub. No.: WO2010/060989
PCT Pub. Date: Jun. 3, 2010

(65) Prior Publication Data
US 2011/0294745 A1  Dec. 1, 2011

(30) Foreign Application Priority Data
Nov. 27, 2008  (DE) .................. 10 2008 059 201

(51) Int. Cl.
| | | |
|---|---|---|
| A61K 38/00 | (2006.01) | |
| A61P 9/10 | (2006.01) | |
| A61P 27/02 | (2006.01) | |
| A61K 9/08 | (2006.01) | |
| A61K 9/00 | (2006.01) | |
| A61K 47/10 | (2017.01) | |
| A61K 47/26 | (2006.01) | |

(52) U.S. Cl.
CPC .............. *A61K 9/08* (2013.01); *A61K 9/0048* (2013.01); *A61K 47/10* (2013.01); *A61K 47/26* (2013.01)

(58) Field of Classification Search
CPC .... A61K 9/146; A61K 9/5084; A61K 9/0048; A61K 47/10; A61K 9/0051; A61K 47/26; A61K 9/08; A61K 9/107; B82Y 5/00
See application file for complete search history.

(56) References Cited

U.S. PATENT DOCUMENTS

| | | | |
|---|---|---|---|
| 4,000,263 A * | 12/1976 | Hebborn .......................... 514/29 |
| 5,192,535 A | 3/1993 | Davis et al. | |
| 5,817,630 A * | 10/1998 | Hofmann ............. A61K 9/0048 514/20.8 |
| 2006/0182771 A1* | 8/2006 | Dor et al. ..................... 424/400 |
| 2006/0240063 A9* | 10/2006 | Hunter et al. ................ 424/423 |

FOREIGN PATENT DOCUMENTS

| | | |
|---|---|---|
| DE | 40 03 844 A1 | 8/1990 |
| DE | 694 02 022 T2 | 7/1997 |
| EP | 0 488 181 A1 | 6/1992 |
| EP | 0 650 730 A1 | 5/1995 |
| WO | WO 95/27481 A1 | 10/1995 |
| WO | WO 95/29677 A1 | 11/1995 |
| WO | WO 99/08684 A2 | 2/1999 |
| WO | WO 02/05815 A1 | 1/2002 |
| WO | WO 0205815 A1 * | 1/2002 |
| WO | WO 2006/133510 A1 | 12/2006 |
| WO | WO 2008/101344 A1 | 8/2008 |

OTHER PUBLICATIONS

Hauser, Biochimica et Biophysica Acta, 2000, 1508, 164-181.*
Rapamycin | The Merck Index Online, available online at https://www.rsc.org/Merck-Index/monograph/m9502/rapamycin?q=authorize, accessed on May 7, 2015.*
Dubbs et al., J. Chem. Eng. Data, 1998, 43, 590-591.*
Prajapati et al., J. Excipients and Food Chem. 2 (3) 2011, 73-88.*
Vocabulary.com, miscible—Dictionary Definition, accessed online on Aug. 20, 2016 at: https://www.vocabulary.com/dictionary/miscible.*
"Partition Coefficient," Wikipedia, http://en.wikipedia.org/wiki/Partition_coefficient, accessed Apr. 16, 2013.
Biocompatible Definition, (http://www.merriam-webster.com/medlineplus/biocompatible), accessed Apr. 16, 2013.
Anderson, D.M., et al., eds., Dorland's Illustrated Medical Dictionary, 28 ed., W.B. Saunders Company, Philadelphia, 1994, pp. 70, 108.
Chen, C.C., et al., "Human Corneal Epithelial Cell Viability and Morphology after Dilute Alcohol Exposure," Investigative Ophthalmology & Visual Science, 43(8): 2593-2602, 2002.
Smith, A.D., et al. eds., Oxford Dictionary of Biochemistry and Molecular Biology, Oxford University Press, New York, 1997, p. 70.
Anness, B. J., and C. W. Bamforth. "Dimethyl sulphide—a review." Journal of the Institute of Brewing 88.4 (1982): 244-252.
BASF Pharma Ingredients & Services 2010, SOLUTOL® HS 15 Technical Information.
Clariant Produkte (Deutschland) GmbH, 2012, Specification Sheet for DME500 poly(ethylene glycol) dimethyl ether.
Lee, Peter A., Stephen J. de Mora, and Maurice Levasseur. "A review of dimethylsulfoxide in aquatic environments." Atmosphere—Ocean 37.4 (1999): 439-456.
Luschmann, Christoph, et al. "Ocular delivery systems for poorly soluble drugs: An in-vivo evaluation." International journal of pharmaceutics 455.1 (2013): 331-337.
Survase, S. A., et al. "Cyclosporin A—a review on fermentative production, downstream processing and pharmacological applications." Biotechnology advances 29.4 (2011): 418.

(Continued)

*Primary Examiner* — Hasan Ahmed
*Assistant Examiner* — Kaipeen Yang
(74) *Attorney, Agent, or Firm* — Bowditch & Dewey, LLP; Roger P. Zimmerman

(57) ABSTRACT

The present invention relates to a solution containing at least one water-miscible biocompatible solvent and a lipophilic substance dissolved therein, wherein upon contact with aqueous body fluid the dissolved lipophilic substance is precipitated out of the solution in the form of nanoparticles and a nanosuspension is formed.

15 Claims, No Drawings

(56) References Cited

OTHER PUBLICATIONS

Gel Definition, IUPAC (International Union of Pure and Applied Chemistry) Compendium of Chemical Terminology, 2nd ed. (the "Gold Book"). Compiled by A. D. McNaught and A. Wilkinson. Blackwell Scientific Publications, Oxford (1997). XML on-line corrected version: http://goldbook.iupac.org (2006-) created by M. Nic, J. Jirat, B. Kosata; updates compiled by A. Jenkins. ISBN 0-9678550-9-8. doi:10.1351/goldbook. Last update: Feb. 24, 2014; version: 2.3.3. DOI of this term: doi:10.1351/goldbook.G02600. Accessed Apr. 16, 2015.

Patravale, V.B., et al., Nanosuspensions: A promising drug delivery strategy, J. Pharmacy & Pharmacology, 2004, 56:827-840.

About the IUPAC Compendium of Chemical Terminology (Gold Book), http://goldbook.iupac.org/about.html, visited Nov. 13, 2015.

Colloidal, IUPAC. Compendium of Chemical Terminology, 2nd ed. (the "Gold Book"). Compiled by A. D. McNaught and A. Wilkinson. Blackwell Scientific Publications, Oxford (1997). XML on-line corrected version: http://goldbook.iupac.org (2006-) created by M. Nic, J. Jirat, B. Kosata; updates compiled by A. Jenkins. ISBN 0-9678550-9-8. doi:10.1351/goldbook <http://dx.doi.org/10.1351/goldbook>. Last update: Feb. 24, 2014 <history.html>; version: 2.3.3 <history.html>. visited Nov. 13, 2015.

Colloid, Wikipedia, https://en.wikipedia.org/wiki/Colloid, visited Nov. 12, 2015.

Emulsion, IUPAC. Compendium of Chemical Terminology, 2nd ed. (the "Gold Book"). Compiled by A. D. McNaught and A. Wilkinson. Blackwell Scientific Publications, Oxford (1997). XML on-line corrected version: http://goldbook.iupac.org (2006-) created by M. Nic, J. Jirat, B. Kosata; updates compiled by A. Jenkins. ISBN 0-9678550-9-8. doi:10.1351/goldbook. Last update: Feb. 24, 2014; version: 2.3.3. visited Nov. 12, 2015.

Emulsion, Wikipedia, https://en.wikipedia.org/wiki/Emulsion, visited Nov. 11, 2015.

International Union of Pure and Applied Chemistry, Wikipedia, https://en.wikipedia.org/wiki/International_Union_of_Pure_and_Applied_Chemistry, visited Nov. 13, 2015.

Suspension, IUPAC. Compendium of Chemical Terminology, 2nd ed. (the "Gold Book"). Compiled by A. D. McNaught and A. Wilkinson. Blackwell Scientific Publications, Oxford (1997). XML on-line corrected version: http://goldbook.iupac.org (2006-) created by M. Nic, J. Jirat, B. Kosata; updates compiled by A. Jenkins. ISBN 0-9678550-9-8. doi:10.1351/goldbook <http://dx.doi.org/10.1351/goldbook>. Last update: Feb. 24, 2014 <history.html>; version: 2.3.3 <history.html>. visited Nov. 13, 2015.

Chemical Composition, Wikipedia, https://en.wikipedia.org/wiki/Chemical_composition, accessed Jul. 29, 2016.

Meena, A. K., Sharma, K., Kandaswamy, M. U. R. U. G. E. S. H., Rajagopal, S., & Mullangi, R. (2012). Formulation development of an albendazole self-emulsifying drug delivery system (SEDDS) with enhanced systemic exposure. Acta Pharm, 62, 563-580.

CAPMUL®—ABITEC, [product lines summary] http://www.abiteccorp.com/product-lines/capmul, visited Nov. 18, 2016.

Hao, J., Gao, Y., Zhao, J., Zheng, J., Li, Q., Zhao, Z., & Liu, J. (2015). Preparation and optimization of resveratrol nanosuspensions by antisolvent precipitation using box-behnken design. *AAPS PharmSciTech*, 16(1), 118-128.

Liu, Y., Sun, C., Hao, Y., Jiang, T., Zheng, L., & Wang, S. (2010). Mechanism of dissolution enhancement and bioavailability of poorly water soluble celecoxib by preparing stable amorphous nanoparticles. *Journal of Pharmacy & Pharmaceutical Sciences*, 13(4), 589-606.

Mansouri, M., Pouretedal, H. R., & Vosoughi, V. (2011). Preparation and characterization of Ibuprofen nanoparticles by using solvent/antisolvent precipitation. In *Open Conf. Proc. J* (vol. 2, pp. 88-94).

"Miscibility," Wikipedia, https://en.wikipedia.org/wiki/Miscibility, visited Dec. 1, 2016.

Prajapati, H. N., Patel, D. P., Patel, N. G., Dalrymple, D. D., & Serajuddin, A. T. (2011). Effect of difference in fatty acid chain lengths of medium-chain lipids on lipid-surfactant-water phase diagrams and drug solubility. Journal of Excipients and Food Chemicals, 2(3), 73-88. Color Copy.

Strickley, R. G. (2004). Solubilizing excipients in oral and injectable formulations. *Pharmaceutical research*, 21(2), 201-230.

Viçosa, A., Letourneau, J. J., Espitalier, F., & Re, M. I. (2012). An innovative antisolvent precipitation process as a promising technique to prepare ultrafine rifampicin particles. *Journal of Crystal Growth*, 342(1), 80-87.

\* cited by examiner

SOLUTIONS OF LIPOPHILIC SUBSTANCES, ESPECIALLY MEDICINAL SOLUTIONS

CROSS-REFERENCE TO RELATED APPLICATIONS

This application is a national stage application under 35 U.S.C. §371 of International Application No. PCT/EP2009/065982, filed Nov. 27, 2009, which claims the benefit of German patent application No. 10 2008 059 201.3, filed Nov. 27, 2008. The entire contents of each of the aforementioned applications are incorporated by reference herein in their entirety.

The present invention relates in particular to medicament formulations for lipophilic poorly water-soluble substances, preferably medicinal agents, which can be applied locally or systemically on or in the human or animal body. Parenteral and oral applications are possible in this case. The system is particularly well suited for topical application, in particular to the eye.

Highly potent active agents are available for numerous disorders. However, these are often very lipophilic and thus poorly water-soluble. This property of low solubility can be defined according to the European Pharmacopoeia by means of the proportions by mass of solvent that is required for the production of a solution of one part by mass (European Pharmacopoeia 5.0/1.04.00.00). In this context a distinction is made between:

poorly soluble
  100 to 1000 parts solvent are required per part substance
very poorly soluble
  1000 to 10000 parts solvent are required per part substance
practically insoluble
  over 10000 parts solvent are required per part substance.

Numerous proposals are known for the solubilising and administration of poorly soluble lipophilic pharmaceutical active agents.

Thus, there are proposals for the production of stable solutions of the respective active agents for oral administration, wherein the active agent should be kept stable in solution by using selected solvent systems and by adding solubilisers. Examples of this are to be found in patent documents DE 40 03 844 A1, EP 0 488 181 A1, EP 0 650 730 A1, WO 95/29677 A1 and WO 99/08684 A2.

DE 40 03 844 A1 relates in particular to the avoidance of ethanol for the production of a liquid pharmaceutical composition containing cyclosporin as active agent.

EP 0 488 181 A1, EP 0 650 730 A1 and also WO 95/29677 A1 relate to solvent systems specially adapted to specific active agents such as nifedipine, rapamycin or camptothecin. According to WO 95/29677 A1 the stable solution obtained can also be injected parenterally. The solvent systems described here can contain, amongst others, polyethylene glycol as a co-solvent or as a dissolution enhancer. The aim is to keep the active agent stable in solution, precipitation of the active agent at the application site is not intended.

DE 694 02 022 T2 describes a stabilised medicament solution for the parenteral application of active agents that are subject to a catalysed breakdown by carboxylate ions. A mixture of a solvent and a non-ionic solubiliser is proposed for the solubilisation, wherein polyethylene glycol can be used as solvent. The solubiliser ensures that a stable solution is obtained. Precipitation of the active agent is not desired.

U.S. Pat. No. 4,000,263 describes a storable liquid preparation for treating acne, wherein erythromycin is present as active agent in a solvent mixture composed of propylene glycol, ethyl alcohol and an ethoxylated ether of lauryl alcohol. The site to be treated is rubbed with the solution, wherein the active agent remains on the site after evaporation of the readily volatile constituents.

WO 2006/133510 A1 relates to a formulation for the parenteral administration of docetaxel or a pharmaceutically active salt thereof. The solvent mixture to be used and additives thereof are also selected here in such a manner that the active agent remains stable in solution. Precipitation is not desired.

WO 2008/101344 A1 relates to a composition that contains lipophilic bioactive compounds such as coenzyme Q10 in particular in solution. The composition can be used for medicinal, cosmetic or food applications. The active agent is mixed with a non-ionic emulsifier and melted and the melt is stirred into water to form a clear solution. Polyethylene glycol is used here as stabiliser for the lyophilisation, but not as solvent.

A problem with lipophilic, poorly soluble to practically insoluble substances used as part of a therapy is the low availability of the active agent at the action site in dissolved form. This is of outstanding importance, since generally only the substance dissolved in the aqueous biological medium is capable of reaching its target structure such as receptors on the cell surface, for example.

Moreover, problems result with respect to the transport of poorly soluble substances through biological barriers such as the intestinal wall after oral application or the cornea in the case of application to the eye, since generally only the dissolved substance is capable of diffusing through cells and tissue and involving low concentrations, small gradients and thus a low mass flow of the substance.

A fundamental requirement for avoiding the problems outlined above is that the substances are brought to the application site in a suitable dosage form so that they are present there in as homogeneous a form as possible, i.e. are evenly distributed. This ensures that as high a concentration as possible is obtained quickly and with lasting effect within the confines of solubility.

Numerous methods are known to the person skilled in the art to achieve this aim. The simplest strategy is to dissolve the active agent in oils such as e.g. liquid triglycerides such those found in numerous vegetable oils or as known as neutral oil under the brand name Miglyol. While such solutions can be applied to the eye as well as parenterally, i.e. in the form of injections, for example, they have the disadvantage that they release the medicinal agent only poorly into the aqueous medium. Moreover, problems can result with the compatibility with the tissue at the application site. The application of oily solutions is frequently accompanied by inflammatory reactions. With respect to application to the eye, an impairment to vision results in some instances because of blurring, which is attributable to the fact that the oil does not mix with the tear fluid. Moreover, the residence time on the eye is inadequate.

To improve the availability of the medicinal agent a possibility specially for applications to the eye is to use ointments in the meaning of the Pharmacopoeia (European Pharmacopoeia 5.0, Semi-solid preparations for cutaneous application 5.0/0123 and Semi-solid preparations for application to the eye 5.0/1163). While their residence time on the eye is increased, their sterile production requires an aseptic production procedure, which greatly increases costs compared to a solution that can be sterile-filtered. Moreover, these preparations are associated with a very low compliance, since the patient must endure the feeling of a foreign body and a substantial temporary vision impediment as a result of blurring. Moreover, the parenteral application of such systems often fails because of the viscosity of the systems, which prevents passage through a cannula.

"Solubilisers" endeavour to bypass the use of lipophilic carriers such as oils or in some instances also ointments for lipophilic substances by the substance being surrounded by the solubiliser. The solubility of poorly soluble substances in water is improved by the hydrophilic surface of these aggregates thus obtained. Cyclodextrins and surface-active substances, so-called surfactants, provide this possibility of improving the solubility, for example. However, solutions with a very short residence time on the eye and thus a low resorption ultimately result from this.

Colloidal carrier systems are a further attempt to obtain usable active agent levels. However, micellar formulations provide too low a storage stability and durability, liposomal preparations are too costly to develop and produce. Both variants, if sterile filtered at all and then only to some degree, and other sterilisation processes such as autoclaving or radiosterilisation would stress the medicinal agents too heavily, which also makes a costly aseptic production unavoidable here.

Suspensions or nanosuspensions of lipophilic medicinal agents provide the possibility of meeting the requirements for application outlined above in that they ensure a "fine" and homogeneous distribution of the medicinal agent at the application site. However, this is subject to an extremely complex production. An additional consideration in the case of suspensions in particular is the low storage stability because of agglomeration or sedimentation, which must be suppressed for a long as possible at high expense.

Emulsions pose the most promising possibility of packaging and applying lipophilic medicinal agents thus far. With Restasis® an eyedrops preparation is already on the market in America that delivers effective active agent levels on application several times a day. However, high production and development costs as well as inadequate durability and stability of the system in the presence of water also pose a problem here. A further disadvantage is that the patient must prepare the preparation, as in the case of Restasis®, for example, for application him/herself and redisperse the emulsion, so that success of the therapy depends on the correct preparation and application of the patient.

Therefore, a desirable formulation is one that dissolves the lipophilic substances, but does not resort to oily solvents for this that are not miscible in water. After application the system should be sufficiently miscible with water at the application site that it releases the medicinal agent fully and spatially evenly. Moreover, the system should be inexpensive to produce e.g. by being able to be sterile filtered as solution by filtration. Such a system would ensure a high ease of application in the therapy since it would be easily applied both parenterally by injection or to the eye by drops without blurring and to be readily tolerable for the organism.

With respect to a uniform distribution of a medicinal agent at an application site, suspensions of nanoparticles of a lipophilic substance with a size of less than 10 µm meet the abovementioned requirements. Because of their large surface area nanoparticles assure a high rate of dissolution and thus improved bioavailability of the applied substance.

However, apart from this nanosuspensions have serious disadvantages. They are complex in production, the processes substantially increase the expense of development and production of such systems and the stability is limited because of an aggregation tendency and growth in particle size, for example.

Therefore, it was an object of the present invention to provide an improved system that meets the abovementioned requirements, with which the bioavailability of lipophilic substances on or in the human or animal body can be increased and facilitated, and that can be obtained in a simple, cost-saving manner, e.g. by means of sterile filtration.

This object is achieved according to the invention by a solution, which contains at least one water-miscible biocompatible solvent and at least one lipophilic substance dissolved therein, wherein upon contact with aqueous body fluid on or in the human or animal organism the solution forms a nanosuspension, in which the at least one lipophilic substance is present in the form of nanoparticles in suspension.

The present invention utilises the advantages of a nanosuspension, i.e. the very finely dispersed particles, but separates these from the disadvantages intrinsic to nanosuspensions indicated above. The solution according to the invention is highly suitable for the administration of lipophilic substances to humans and animals. The administration can be oral, parenteral or topical. In particular the solution according to the invention is highly suitable for parenteral application and for the application of lipophilic substances to the eye.

The present invention is based on the principle that upon contact with water the solution with the lipophilic substance releases the dissolved substance to form defined nanostructures, which because of their very large surface area and their uniform distribution provide improved reception conditions for poorly water-soluble active agents.

For this, the lipophilic substance is processed with a solvent that is miscible with water to form a genuine, i.e. in particular molecularly disperse, stable solution. The suspension of the lipophilic substance is formed spontaneously at the application site only upon incorporation of this solution as a result of water, which acts as so-called antisolvent, extracting the solvent from the mixture, as it were. The solution according to the invention can be used wherever an aqueous liquid is present. This is the case in the organisms of humans and animals, which contain water in sufficient quantity. For example, in the case of application to the eye the in situ precipitation of the active agent can be activated by contact with the tear fluid.

Therefore, it is possible with the present invention to apply lipophilic substances as solutions without resorting to "oily" solvents or other lipophilic solvents such as triglycerides or cholesterol. These oily or lipophilic solvents are solvents, which in contrast to the solvent used according to the invention are not miscible in water, but form an emulsion, i.e. a two-phase system, when mixed with water.

Solvents that are miscible with water and in particular form a homogeneous system with water are used according to the invention.

Solvents suitable for the invention can completely dissolve the lipophilic substances so that a genuine solution is formed. The solvents should preferably be physiologically compatible and not toxic. It is particularly preferred that they should be transparent. They should be liquid and preferably have a melting point close to or lower than body temperature of about 37° C.

Examples of suitable solvents are e.g. polyethylene glycol (PEG) and derivatives thereof such as e.g. alkyl ether, as well as glycerol, propylene glycol, dimethyl sulphoxide (DMSO), N-vinylpyrrolidone as well as solvents such as those described, for example, in WO 95/27481 A1 for the production of liquid polymer solutions for the delayed release of active agents.

Mixtures of two or more of these solvents can also be used.

Polyethylene glycols, propylene glycol and N-vinylpyrrolidone are particularly preferred.

Polyethylene glycols or derivatives thereof that are suitable as solvents have in particular a molar mass in the range of 50 to 100 000 Da, preferably from 100 to 1000 Da and particularly preferred 200 to 600 Da. Polyethylene glycols are particularly preferred with a molar mass with which the polyethylene glycols are present in liquid form in the region of body temperature of about 37° C. Examples of derivatives of polyethylene glycol are the mono and diethyl ethers thereof.

The higher molecular solid polyethylene glycols can be used, for example, in mixture with liquid polyethylene glycols or other liquid solvents.

The present invention is suitable in principle for all lipophilic substances such as lipophilic pharmaceutical active agents in particular such as medicinal agents. Lipophilic substances that are poorly soluble to practically insoluble in water can thus be applied successfully. In particular, the present invention is also suitable for very poorly water-soluble to practically water-insoluble active agents. Examples of these are substances such as cyclosporin A, budesonide, beclomethasone, triamcinolone acetonide, dexamethasone, fluticasone dipropionate.

If the solution according to the invention with the dissolved substance comes into contact with water, interactions occur and the solvent mixes with water, and the resulting decreasing solubility for this substance causes extremely small solid particles of the lipophilic substance to precipitate out.

The solid particles, i.e. the nanoparticles, generally have a size in the range of up to 10 μm. Particles with a size in a range of up to 1 μm are preferred and particles with a size of less than 1 μm are particularly preferred. Particles with as small a particle size as possible are particularly suitable for the application according to the invention. Thus, particles with a size of few nanometers, e.g. of 1 nm, can be used, for example.

The particles obtained can have an irregular surface and shape. Therefore, the size relates to the main axis of the particles, i.e. the axis with the largest extent.

The presence of nanoparticles in the suspension and determination thereof can be achieved by means of methods known per se, e.g. by means of laser diffractometry and photon correlation spectroscopy.

The properties of the solution according to the invention and of the nanoparticles can be varied or adjusted in a variety of ways according to the requirements of a specific application. In this case, principles and agents can be applied that are known per se to the formulation scientist for the formulation of liquid medicinal agents.

Thus, the precipitation of the nanoparticles out of the solution can be controlled by incorporating one or more surfactants (surface-active substances). Physiologically compatible surfactants are preferably used for the present invention. Examples of these are cetyl alcohol, stearyl alcohol, sodium cetyl stearyl sulphate, glycerol monostearate and sorbitan fatty acid ester. It is particularly preferred if surfactants are used such as occur in the physiological medium of the human and animal organism such as e.g. lecithin, cholesterol, phosphatidylcholine, phosphatidylserine, phosphatidylinositol and phosphatidylethanolamine.

For this, the solution properties of the solvent can also be varied by adding a co-solvent, wherein a change in particle size can be achieved depending on the combination.

Amphiphilic phospholipids such as e.g. diheptanoyl glycerophosphocholine (DHGPC), a phosphatidylcholine that does not occur physiologically, can also be used that can also act as co-solvent.

A possibility of controlling the particle size lies in influencing the particle growth by means of the physicochemical properties of the solution according to the invention with the substance dissolved therein. One of these properties is viscosity. A diffusion-limited aggregation of the particles can be achieved by increasing the viscosity of the system. In this case, fractal structures, i.e. particles with high surface irregularity, occur that are thus distinguished by a particularly large surface.

Viscosity-enhancing agents, for example, that are known to the formulation scientist for parenteral application can be added to the solution according to the invention for increasing the viscosity. Examples of this are viscosity-enhancing polymers and also polyethylene glycol, cellulose ether, polyvinylpyrrolidone and polyvinyl alcohol.

Some substances can form inclusion compounds with the nanoparticles by surrounding the nanoparticles. The particle size can also be adjusted by the formation of such inclusion compounds, since a growth and the agglomeration of the particles can be prevented by this. An example of such a substance is polyvinylpyrrolidone, which simultaneously acts as viscosity-enhancing agent.

Depending on the application or solvent system, it can be advantageous if the nanoparticles formed reside for as long as possible at the release site in order to increase the resorption rate. This can be achieved, for example, by reducing the mobility of the nanoparticles.

The mobility of the nanoparticles can be caused, for example, by adding viscosity-enhancing agents or by optimising the electrostatic attraction forces.

The aforementioned viscosity-enhancing agents can be used, for example, to increase the viscosity.

The electrostatic interaction of the nanoparticles with the tissue at the application site can be used to reduce the mobility of the nanoparticles.

For example, the zeta potential of the nanoparticles can be adjusted in opposite direction to the potential of the tissue. The opposite potential can be a substance property of the nanoparticles per se. Additives such as e.g. phosphates or citrates can be added to adjust the zeta potential. Such additives for adjusting the zeta potential are known to the person skilled in the art as peptising agents, for example.

A wide variety of compositions of the solvent system according to the invention can be obtained on the basis of the above principles.

Examples of different embodiments are specified below, by means of which it is demonstrated how the properties of the solvent system according to the invention or the nanoparticles can be varied by combining one or more additives and auxiliary agents.

1. The simplest variant is a binary formulation of a solvent that is suitable according to the invention with a lipophilic substance. The solvent properties can be varied by adding a co-solvent, wherein desired particle sizes can be obtained in dependence on the respective combination.

2. More possibilities for influencing and controlling the formation, size and functionality of the nanoparticles can be obtained with ternary systems, which in addition to the solvent or solvent mixture and the lipophilic substance contain further additives or auxiliary agents.

a) The growth process of the nanoparticles can be influenced by adding surfactants or other amphiphilic substances.

b) The particle growth and the diffusion of the precipitated nanoparticles can be slowed down by adding viscosity-enhancing agents.

Substances that gel in situ can also be used to increase viscosity. In the case of the substances that gel "in situ" gelling occurs only at the application site by changing the ambient conditions such as the pH value, the temperature, the shear stress or other external influences.

c) The removal of the nanoparticles can be slowed down by varying the zeta potential. Agents for adjusting the zeta potential, which can positively adjust the zeta potential of the nanoparticles, can preferably be used for this.

d) A functionalisation of the nanoparticles or the entire system of the formulations described above under 2a to c) can be achieved by suitable selection of the amphiphilic or viscosity-enhancing agents.

i) Thus, when using charged surfactants, the nanoparticles enclosed by these can be fixed to oppositely charged surfaces for a longer period in dependence on the charge.

ii) By using charged viscosity-enhancing agents or substances that gel in situ, the entire system can be retained on oppositely charged surfaces for specific periods.

3. Working from the abovementioned embodiments in 1. and 2., still further variables, and thus an increased specificity and effectiveness, can be introduced into the system by quaternary formulations.

a) Thus, two different amphiphilic substances can be added to a solution according to 1). Depending on the combination and properties of these amphiphilic substances such as charge, size of the lipophilic part etc., the effects described for the surfactants according to 2a) can be amplified or optimised.

b) The presence of a surfactant in the embodiment according to 2a) allows small proportions of water to be worked into the formulation, which thus assists the spontaneous precipitation reaction upon contact with water at the application site.

c) A high effectiveness can be achieved by adding a combination of viscosity-enhancing agents and surfactants to the embodiment according to 1. Here, the nanoparticles can reside, charged or uncharged, finely distributed and bound in a gel-like state for longer on surfaces and release the active agent more effectively. A viscosity-enhancing agent or a substance that gels in situ can be added to increase viscosity.

The embodiments outlined above are understood to merely be examples for illustration of the wide variety of possibilities of variation that the solution according to the invention offers. The abovementioned additives and also further additives well known to the formulation scientist can, of course, be added in any combination as required to the fundamental embodiment according to 1.

When the solution of the invention is used according to the invention a precipitate of the previously dissolved active agent in the form of nanoparticles is formed upon contact with aqueous liquids, since the solubility of the active agent is reduced when solvents are mixed with water. The particle size can be kept as small as possible either by the amphiphilic additives that become "active" during this, by viscosity-enhancing additives or a combination thereof and agglomerates can be prevented.

The present invention thus relates to a nanosuspension occurring in situ with different adjustable functionalities or the resulting nanoparticles, and thus combines the advantages of a genuine solution with the advantages of a nanosuspension without including the disadvantages of the two therein. Thus, the invention constitutes an inexpensive to produce product that can be sterile-filtered with improved application and resorption, as a result of which a higher bioavailability is achieved.

The solution according to the invention is suitable in particular for the production of a pharmaceutical composition for the topical, oral or parenteral administration of pharmaceutical substances.

The solution according to the invention is preferably used for the topical or parenteral administration of pharmaceutical active agents. It is particularly preferred if the solution according to the invention constitutes a pharmaceutical composition for the administration of a pharmaceutical active agent to the eye.

It is understood that where required for the production of a pharmaceutical composition based on the solution according to the invention, the pharmaceutical composition can additionally contain further auxiliary agents, as known to the formulation scientist for the respective application.

The principle of the present invention as well as the production of the solution according to the invention is illustrated further on the basis of examples below.

EXAMPLES

Example 1: Miscibility of Solvent and Water

Polyethylene glycol 400, a clear liquid solvent, was mixed with water in different ratios of 1:10 to 1:1 ($H_2O$:PEG 400) and the resulting solution characterised. The solution was mixed in a vortex mixer at room temperature (21° C.). All the ratios tested resulted in a transparent homogeneous mixture.

Example 2: Solution of Active Agent and Solvent

Polyethylene glycol 400 served as solvent. 20 mg of cyclosporin A (c(CsA)=20 mg/ml) were dissolved in 1 ml of this clear, already slightly more viscous liquid. Dissolution occurred at room temperature (21° C.) with shaking in a vortex mixer. The resulting solution was transparent and free from particles of suspended matter. This was confirmed under a microscope. Clouding formed spontaneously on addition of 100 μl of water to 500 μl of this solution. A coarsely structured precipitate with defined crystals could be observed when viewed under the microscope.

Example 3: Solution of Active Agent, Regulators and Solvent 20 mg of phospholipid (diheptanoyl glycerophosphocholine (DHGPC)) were dissolved in 1 ml of polyethylene glycol 400 in the vortex mixer. This resulted in a clear solution at room temperature (21° C.). 20 mg of cyclosporin A were then dissolved therein in the same conditions. The resulting mixture was transparent and free from particles of suspended matter. Microscope images confirmed this. The addition of 100 μl of water in drops to 500 μl of this solution caused a spontaneous precipitation. When viewed under the microscope, it could be observed that finely distributed structures without recognisable larger crystals had formed.

Example 4: Water Absorption Capacity

A solution of 10 mg of phospholipid and 2 mg of cyclosporin A in 1 ml of polyethylene glycol 400 was produced. Dissolution of the substances occurred in a vortex mixer at room temperature (21° C.). Water was added in drops to this solution in ratios of 1:10 to 3.5:10 (H₂O: solution) and mixed. The system initially clouded. This clouding disappeared shortly thereafter with all ratios up to 3:10 (H₂O:solution) and a transparent solution free from particles of suspended matter resulted. Very finely dispersed particles clearly shielded by a phospholipid layer were evident under the microscope. The mixtures with a higher water content did not clear and a stable precipitate was formed.

The invention claimed is:

1. A pharmaceutical composition consisting essentially of:
at least one water-miscible biocompatible solvent capable of forming a homogenous mixture with water that is selected from the group consisting of polyethylene glycol (PEG), monoethyl ether derivatives of polyethylene glycol, diethyl ether derivatives of polyethylene glycol, glycerol, propylene glycol, N-vinylpyrrolidone and a mixture thereof, and
at least one lipophilic substance dissolved therein,
wherein the lipophilic substance is poorly soluble to practically insoluble in water, wherein the lipophilic substance is a pharmaceutical agent, wherein the pharmaceutical composition has been formulated for administration to the eye of a human or an animal, and wherein a nanosuspension is formed upon contact with aqueous body fluid on or in the eye in which the at least one lipophilic substance is present in the form of nanoparticles in suspension.

2. The pharmaceutical composition according to claim 1, wherein the solution additionally contains an additive selected from the group consisting of a surfactant, a viscosity-enhancing additive, an agent for adjusting the zeta potential of the nanoparticles and a mixture thereof.

3. The pharmaceutical composition according to claim 1, wherein the nanoparticles have a fractal structure.

4. The pharmaceutical composition according to claim 3, wherein the nanoparticles are smaller than 10 µm.

5. The pharmaceutical composition according to claim 1, wherein the nanoparticles have a size of 1 nm or more.

6. A method of administering one or more lipophilic substances selected from at least one pharmaceutical active agent to the eye of a human or an animal comprising: contacting an aqueous body fluid on or in the eye of a human or an animal with a pharmaceutical composition according to claim 1, wherein upon contact with the aqueous body fluid, the pharmaceutical composition forms a nanosuspension in which the lipophilic substance is present in the form of nanoparticles in suspension.

7. The pharmaceutical composition according to claim 1, wherein the lipophilic substance is very poorly water soluble to practically insoluble in water.

8. The pharmaceutical composition according to claim 1, wherein the lipophilic substance is selected from cyclosporine A, budesonide, beclomethasone, triamcinolone acetonide, dexamethasone and fluticasone diproprionate.

9. The pharmaceutical composition according to claim 2, wherein the water-miscible biocompatible solvent is a liquid at about 37° C.

10. The pharmaceutical composition according to claim 2, wherein the additive is a surfactant selected from the group consisting of cetyl alcohol, stearyl alcohol, sodium cetyl stearyl sulphate, glycerol monostearate, sorbitan fatty acid ester, lecithin, cholesterol, phosphatidylcholine, phosphatidylserine, phosphatidylinositol, phosphatidylethanolamine and a mixture thereof.

11. A pharmaceutical composition consisting essentially of:
at least one water-miscible biocompatible solvent capable of forming a homogenous mixture with water that is selected from the group consisting of polyethylene glycol (PEG), monoethyl ether derivatives of polyethylene glycol, diethyl ether derivatives of polyethylene glycol, glycerol, propylene glycol, N-vinylpyrrolidone and a mixture thereof, and
at least one lipophilic substance dissolved therein, wherein the lipophilic substance is a pharmaceutical agent that is poorly soluble to practically insoluble in water, and;
additionally contains diheptanoyl glycerophosphocholine (DHGPC) and at least one additive selected from the group consisting of a surfactant, a viscosity-enhancing additive, an agent for adjusting the zeta potential of the nanoparticles and a mixture thereof;
wherein the pharmaceutical composition has been formulated for administration to the eye of a human or an animal, and wherein a nanosuspension is formed upon contact with aqueous body fluid on or in the eye in which the at least one lipophilic substance is present in the form of nanoparticles in suspension.

12. The pharmaceutical composition according to claim 2, wherein the additive is a viscosity-enhancing agent selected from the group consisting of viscosity-enhancing polymers, polyethylene glycol, cellulose ethers, polyvinylpyrrolidone, polyvinyl alcohol and a mixture thereof.

13. The pharmaceutical composition according to claim 2, wherein the additive is an agent for adjusting the zeta potential of nanoparticles selected from the group consisting of peptizing agents.

14. The pharmaceutical composition according to claim 11 wherein the water-miscible biocompatible solvent is polyethylene glycol and the lipophilic substance is cyclosporine A.

15. The pharmaceutical composition according to claim 11 wherein the water-miscible biocompatible solvent is polyethylene glycol, the lipophilic substance is cyclosporine A, and the additive is diheptanoyl glycerophosphocholine (DHGPC).

* * * * *